United States Patent [19]
Kielpikowski

[11] Patent Number: 5,824,172
[45] Date of Patent: Oct. 20, 1998

[54] METHOD OF MAKING AN ABSORBENT GARMENT COMPRISING DUAL CONTAINMENT FLAPS

[75] Inventor: David Peter Kielpikowski, Appleton, Wis.

[73] Assignee: Kimberly-Clark Worldwide, Inc., Neenah, Wis.

[21] Appl. No.: 834,663

[22] Filed: Apr. 11, 1997

Related U.S. Application Data

[62] Division of Ser. No. 260,659, Jun. 16, 1994, Pat. No. 5,669,896.
[51] Int. Cl.⁶ ........................................................ A61F 13/15
[52] U.S. Cl. ........................ 156/164; 156/163; 156/229; 156/256; 156/267; 604/385.2
[58] Field of Search ............................. 156/164.161, 163, 156/229, 256, 267, 324; 604/385.2

[56] References Cited

U.S. PATENT DOCUMENTS

| | | |
|---|---|---|
| 3,902,236 | 9/1975 | Deem . |
| 4,076,663 | 2/1978 | Masuda et al. . |
| 4,286,082 | 8/1981 | Tsubakimoto et al. . |
| 4,662,877 | 5/1987 | Williams . |
| 5,085,654 | 2/1992 | Buell . |
| 5,176,672 | 1/1993 | Bruemmer et al. . |
| 5,192,606 | 3/1993 | Proxmire et al. . |
| 5,304,159 | 4/1994 | Tanji et al. . |
| 5,304,160 | 4/1994 | Igaue et al. . |
| 5,308,344 | 5/1994 | Toth . |
| 5,342,342 | 8/1994 | Kitaoka . |
| 5,429,632 | 7/1995 | Tanji et al. . |
| 5,509,915 | 4/1996 | Hanson et al. . |

FOREIGN PATENT DOCUMENTS

| | | |
|---|---|---|
| 0657153 | 6/1995 | European Pat. Off. . |
| 40-11543 | 4/1965 | Japan . |
| 40-1543 | 4/1965 | Japan . |
| 41-17377 | 8/1966 | Japan . |
| 2-71521 | 5/1990 | Japan . |
| 3-218752 | 9/1991 | Japan . |
| 4-47428 | 4/1992 | Japan . |
| 4-150853 | 5/1992 | Japan . |
| 4-218157 | 8/1992 | Japan . |
| 4-99921 | 8/1992 | Japan . |
| 5-42180 | 2/1993 | Japan . |
| 5-42181 | 2/1993 | Japan . |
| 2251172 | 7/1992 | United Kingdom . |
| 2255896 | 11/1992 | United Kingdom . |
| 2266055 | 10/1993 | United Kingdom . |
| 2266225 | 10/1993 | United Kingdom . |
| 2266444 | 11/1993 | United Kingdom . |
| 2284537 | 6/1995 | United Kingdom . |
| 2284538 | 6/1995 | United Kingdom . |
| 2284550 | 6/1995 | United Kingdom . |

*Primary Examiner*—Jeff H. Aftergut
*Attorney, Agent, or Firm*—Brinks Hofer Gilson & Lione

[57] ABSTRACT

Disclosed is an absorbent garment including a pair of outer containment flaps and a pair of inner containment flaps, said outer and inner containment flaps being formed from a first integral sheet of containment flap material having a length, said inner containment flaps having a length less than the length of said first sheet of containment flap material. Also described is a method of producing the absorbent garments.

13 Claims, 7 Drawing Sheets

5,824,172

METHOD OF MAKING AN ABSORBENT GARMENT COMPRISING DUAL CONTAINMENT FLAPS

CROSS-REFERENCE TO RELATED APPLICATION

This is a division of application Ser. No. 08/260,659, filed Jun. 16, 1994, now U.S. Pat. No. 5,669,896.

BACKGROUND OF THE INVENTION

The present invention is directed to an absorbent garment and a method for the manufacture thereof. Specifically, the present invention is directed to an absorbent garment having dual containment flaps.

Absorbent garments such as disposable diapers, training pants, adult incontinent garments, and the like, are well known. In order to improve the ability of such absorbent garments to absorb and contain discharged body wastes, it has become common to include on such garments mechanical systems for controlling the movement of such wastes. Such mechanical systems include containment flaps, waist flaps, and leg elastics.

Containment flaps generally comprise a proximal edge attached to the garment and an elasticized distal edge opposite the proximal edge. The containment flaps are attached to the garment such that the distal edges of the containment flaps are maintained in a generally upright position so that the distal edge of the containment flap contacts the body of a wearer thus presenting a lateral barrier to the flow of waste.

Known methods of providing containment flaps generally involve two or more Individual flaps which are separately attached to the garment. This has led to generally complex manufacturing processes that may represent a rate-limiting step with respect to the production of such absorbent garments.

Accordingly, it is desirable to provide an improved containment flap system and an improved process for the manufacture thereof.

SUMMARY OF THE INVENTION

In one aspect, the present invention concerns an absorbent garment. The absorbent garment comprises an outer cover, a bodyside liner, and an absorbent core located between said outer cover and said liner. The garment further comprises a pair of outer containment flaps having a proximal edge attached to said bodyside liner, a distal edge, and a first elastic member adjacent said distal edge. The garment further comprises a pair of inner containment flaps having a proximal edge attached to said bodyside liner, a distal edge and a second elastic member adjacent said distal edge. The outer and inner containment flaps are formed from a first sheet of containment flap material having a length. The inner containment flaps have a length less than the length of said first sheet of containment flap material.

In another aspect, the present invention concerns a method for producing an absorbent garment. The method comprises the steps of providing a first sheet of containment flap material. A pair of first elastic members is attached to said first sheet of containment flap material. A pair of second elastic members is attached to said first sheet of containment flap material. The pair of second elastic members is generally inboard of said pair of first elastic members. A portion of said first sheet of containment flap material is removed between said pair of second elastic members to form a containment flap assembly. The containment flap assembly is attached to a garment chassis to define outer containment flaps and inner containment flaps. The garment chassis comprises an outer cover, a bodyside liner, and an absorbent core located between said outer cover and said bodyside liner.

DETAILED DESCRIPTION OF THE PRESENT INVENTION

The present invention relates to disposable absorbent garments such as diapers, training pants, adult incontinence products, feminine care products, and the like. The term "disposable" refers to absorbent garments which are not intended for reuse, such as by being laundered, but instead are intended to be used for a limited duration of time and then disposed of.

In one aspect, the present invention relates to an absorbent garment. Such an absorbent garment can best be understood from reference to the drawings wherein like numbers represent like elements.

Figure 1:
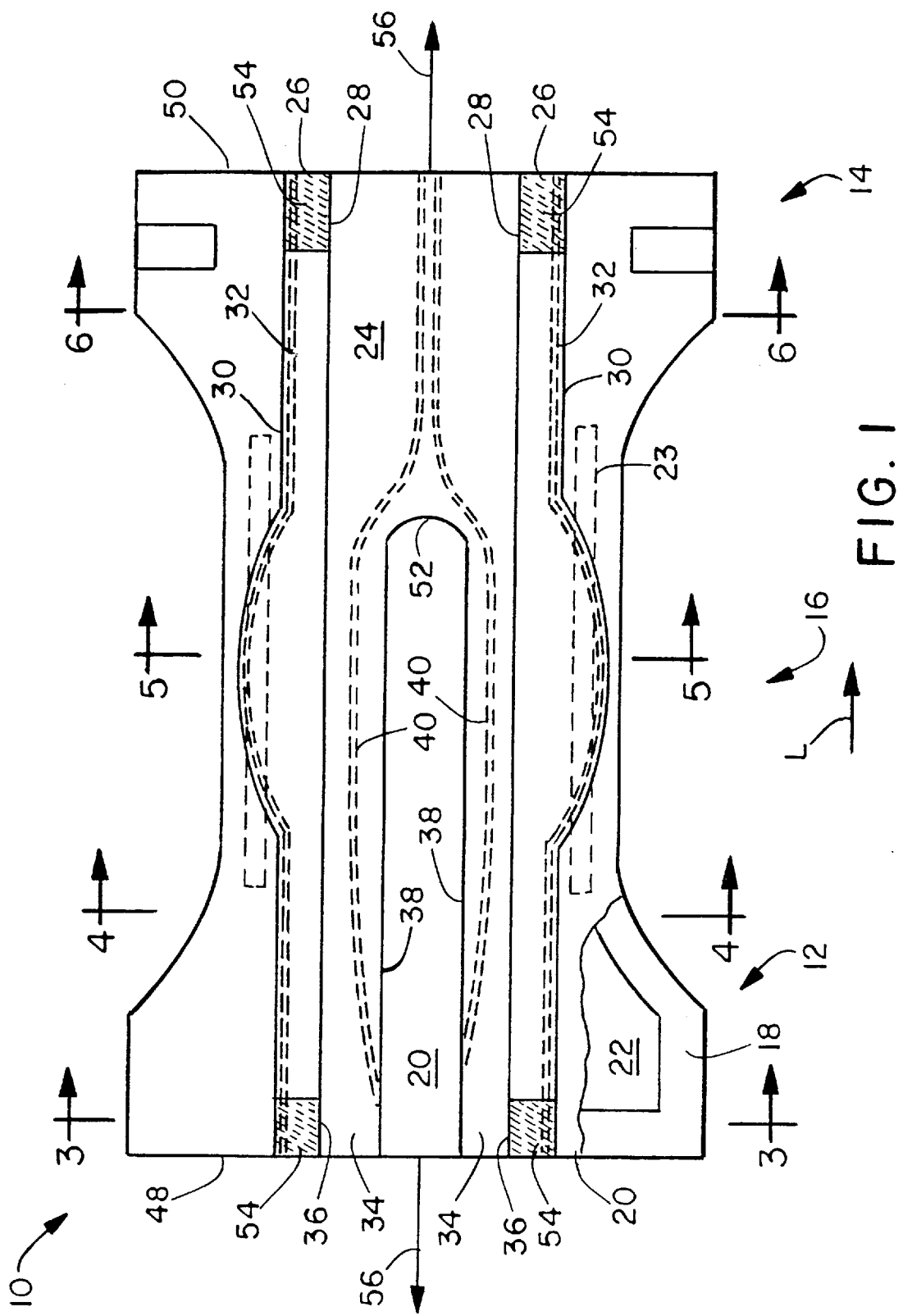
FIG. 1 illustrates a plan view of an absorbent article according to the present invention.
Figure 2:
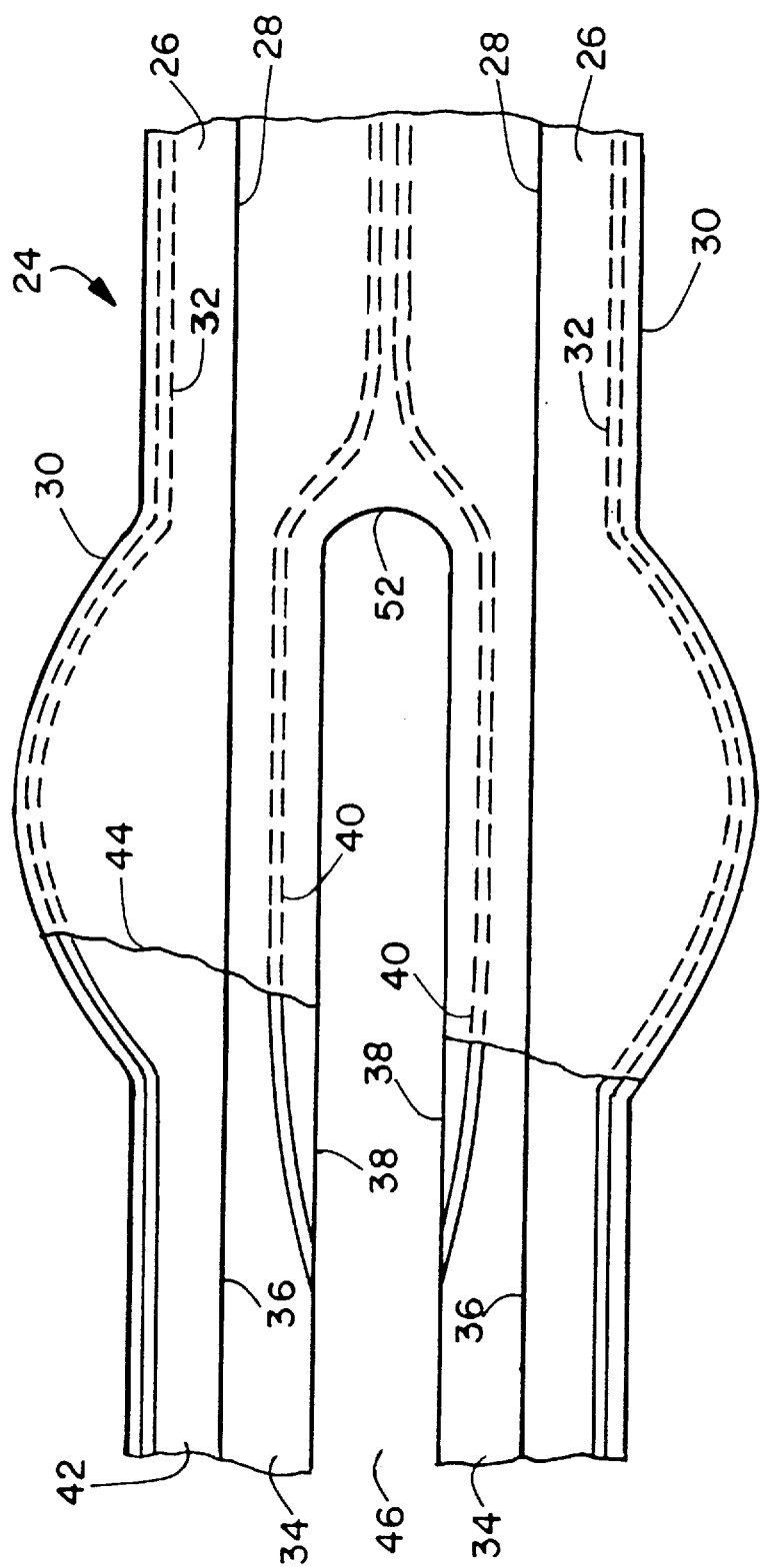
FIG. 2 illustrates a plan view of a containment flap assembly according to the present invention.
Figure 3:
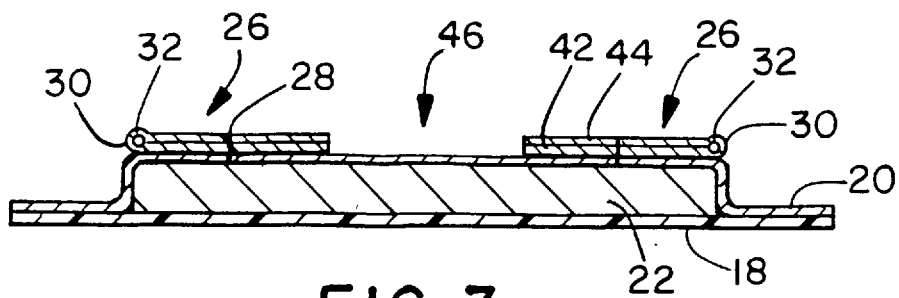
FIG. 3 illustrates a cross-sectional view taken along line 3—3 of FIG. 1.
Figure 4:
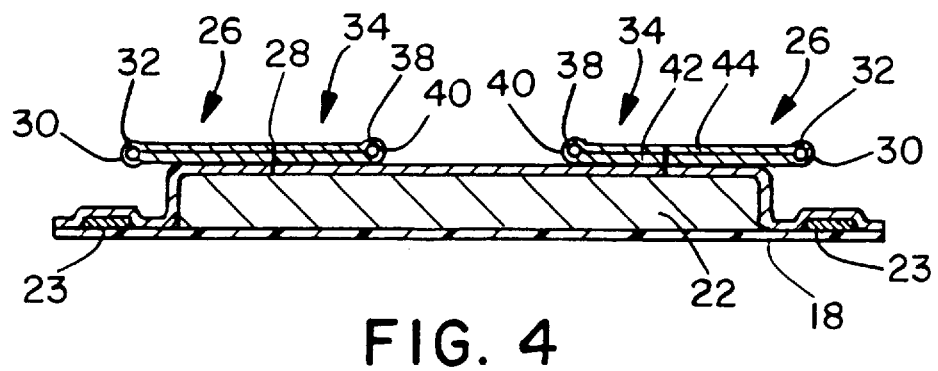
FIG. 4 illustrates a cross-sectional view taken along line 4—4 of FIG. 1.
Figure 5:
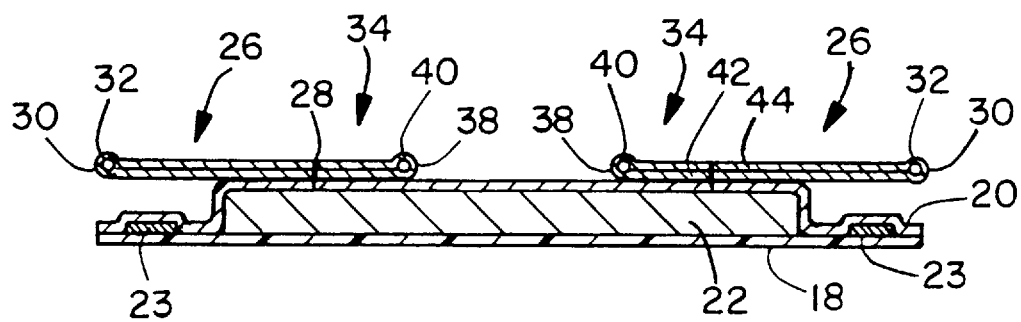
FIG. 5 illustrates a cross-sectional view taken along line 5—5 of FIG. 1.
Figure 6:
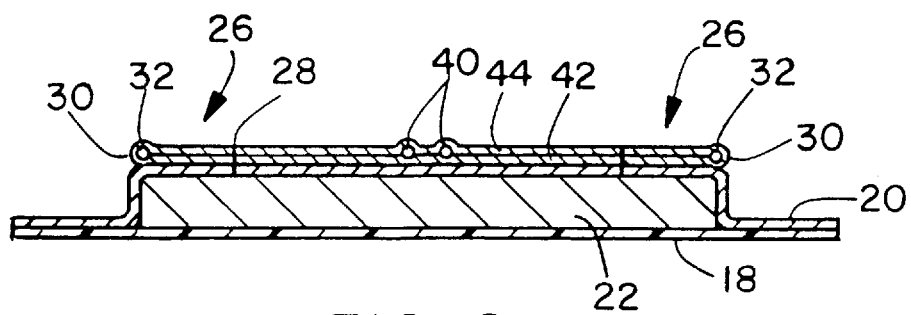
FIG. 6 illustrates a cross-sectional view taken along line 6—6 of FIG. 1.

With reference to the drawings, FIG. 1 illustrates a disposable infant diaper 10. While the present invention will be described with reference to a disposable infant diaper, it is to be understood that the invention is equally applicable to other disposable absorbent garments, such as those described above. Disposable diaper 10 includes a front portion 12, a rear portion 14, and a crotch portion 16 located between the front portion 12 and the rear portion 14. The disposable diaper 10 comprises an outer cover 18, a bodyside liner 20, and an absorbent core 22 located between the outer cover 18 and the bodyside liner 20. The diaper 10 includes leg cuffs 23 and a containment flap assembly 24 attached to bodyside liner 20. The containment flap assembly 24 is illustrated in FIG. 2. With reference to FIGS. 1 and 2, the containment flap assembly comprises a pair of outer containment flaps 26 having proximal edges 28 defined, in the illustrated embodiment, by a line of attachment at which the containment flap assembly is attached to the bodyside liner. The outer containment flaps 26 further comprise distal edges 30 opposite said proximal edges 28 and first elastic members 32 adjacent said distal edges 30.

The containment flap assembly 24 further comprises a pair of inner containment flaps 34. The inner containment flaps 34 have a proximal edge 36, which, in the illustrated embodiment, generally coincides with the proximal edge 28 of the outer containment flaps 26. Again, proximal edge 36 of inner containment flap 34 is that point at which the containment flap assembly 24 is attached to the bodyside liner 20 of diaper 10. The inner containment flaps 34 further comprise distal edges 38 opposite said proximal edges 36 and second elastic members 40 adjacent the distal edges 38.

The outer containment flaps 26 and inner containment flaps 34 are formed from a first integral sheet of containment flap material 42 (FIG. 2) having a length in the direction L. The inner containment flaps 34 have a length, defined by the distal edges 38, which is less than the length of the first sheet of containment flap material 42. Specifically, in the illustrated embodiment, the inner containment flaps are located in said front portion and said crotch portion but not in said rear portion. For example, from about 60 to about 100, preferably from about 70 to about 90 percent of the length of the inner containment flaps 34 is located in the front one-half of the length of the diaper.

In the illustrated embodiment, the containment flap assembly 24 further comprises a second sheet of containment flap material 44 (FIG. 2) attached to said first sheet of containment flap material. The second sheet of containment flap material 44 is superposed on, and generally coincides with, the first sheet of containment flap material 42. The first and second sheets of containment flap material 42, 44 define an opening 46 between the distal edges 38 of inner containment flaps 34. The opening 46 is located in the front portion 12 and crotch portion 16 of the disposable diaper 10. In the illustrated embodiment, the opening 46 is generally U-shaped. Naturally, the opening 46 may have other shapes such as oval, rectangular, and the like. The opening 46 is open at one end. The first and second sheets of containment flap material are laterally continuous in at least a portion of the transverse direction (perpendicular to the direction L) in the rear portion 14 of the diaper 10.

The containment flap assembly 24 is suitably attached to the bodyside liner along two lines of attachment that correspond to the proximal edges of the inner and outer containment flaps. The containment flap assembly may be attached by lines of adhesive, thermal bonding, ultrasonic bonding, or other methods of attachment known to those skilled in the art. Alternatively, the containment flap assembly may be attached to the bodyside liner along four lines of attachment with each line of attachment coinciding with a proximal edge of an inner or outer containment flap. In this embodiment, the proximal edges of the inner and outer containment flaps would not coincide. Still further, the containment flap assembly can be attached to the bodyside liner in any area that is not located between the proximal and distal edges of the inner or outer containment flaps in at least the crotch section.

In the embodiment illustrated in FIGS. 1 and 2, the distal edges 30 are non-parallel to each other, and the first elastic members 32 are non-parallel to each other. Of course, it is to be understood that the first elastic members 32 may be parallel and that the distal edges 30 of the outer containment flaps 26 may similarly be parallel. Further, while the illustrated embodiments employ a single first elastic member in each outer containment flap, it is to be understood that additional elastic members may be present adjacent the first elastic members 32.

Similarly, the second elastic members 40 are generally non-parallel to each other. In the illustrated embodiment, the second elastic members 40 do not extend all the way to the front edge 48 of the disposable diaper 10. The second elastic members 40 do, however, extend substantially all the way to the rear edge 50 of the disposable diaper 10. Specifically, the second elastic members 40 converge toward one another, in the rear portion 14 of the diaper 10, past a terminal edge 52 of the opening 46. Thus, the second elastic members are spaced further apart in said crotch portion than in said rear portion and are immediately adjacent to one another in said rear portion. The second elastic members 40 may terminate at a point spaced from the rear edge 50 of the diaper 10.

Locating the second elastic members immediately adjacent one another in the rear portion of the absorbent garment, and generally in the center of the garment, assists in forming a seal against the flow of solid waste away from the opening 46. Specifically, the second elastic members provide a close, body-conforming fit against the irregular surfaces of a wearer.

The facing surfaces of outer containment flaps 26 are attached to the bodyside liner 20 in attachment areas 54. This assists in allowing the first elastic members 32 to maintain the outer containment flaps 26 in an upright condition when the containment flaps are in a relaxed, untensioned, contracted, gathered condition.

As used herein, reference to the term "outer" and "outboard" is intended to refer to a position most remote, or relatively more remote, from the centerline 56 of the disposable diaper 10 and containment flap assembly 24. Similarly, the term "inner" and "inboard" is intended to refer to a position closest to or relatively closer to the centerline 56.

FIGS. 3–6 illustrate cross-sectional views taken along lines 3—3, 4—4, 5—5, and 6—6, respectively, of FIG. 1.

Figure 7:
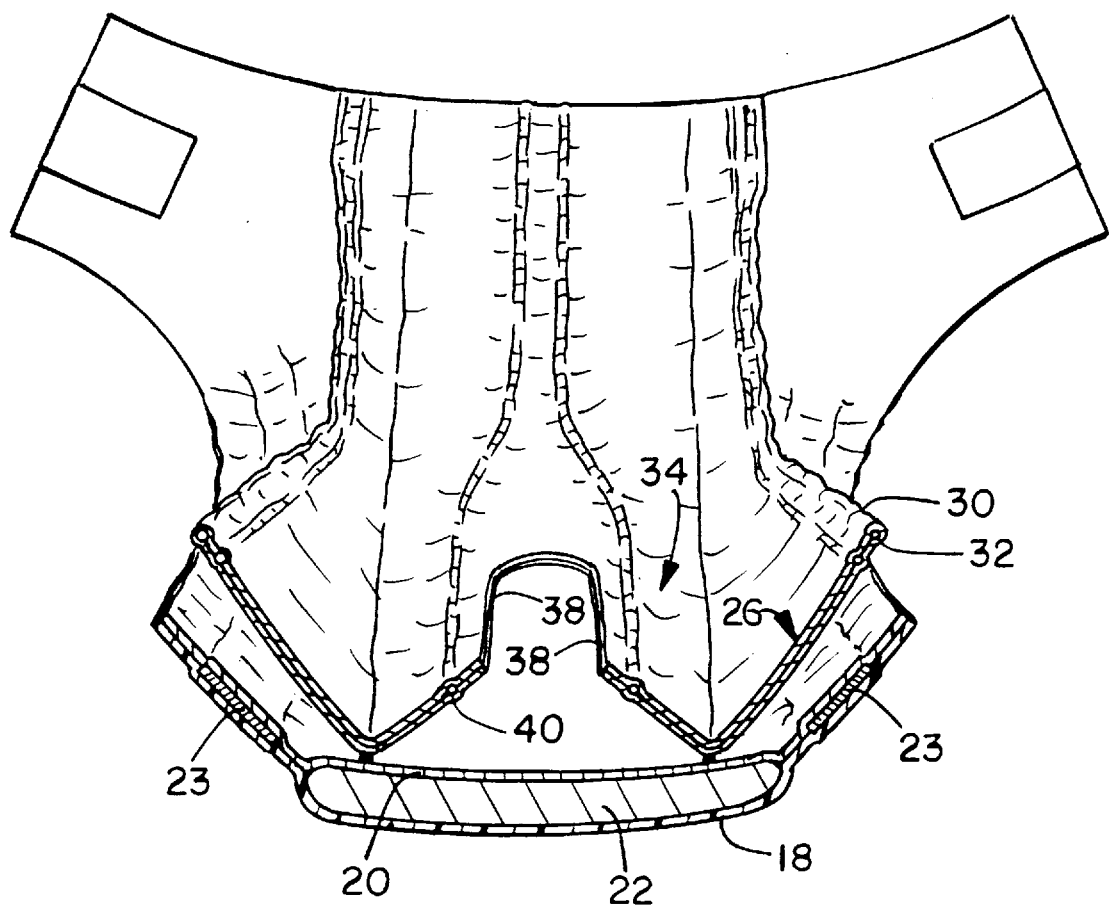
FIG. 7 illustrates a cross-sectional perspective view of the absorbent garment illustrated in FIG. 1 in a relaxed condition.

FIG. 7 illustrates the cross-sectional perspective view of the disposable diaper 10 when in a relaxed non-stretched condition.

Specific examples of materials suitable for use as the first and second sheets of containment flap material include nonwoven materials, such as spunbond or meltblown thermoplastic polymers, such as polyolefins; bonded carded webs; film materials, such as polyolefin, ethylene vinyl acetate, ethyl methacrylate, and polyester films; foam materials, such as polyolefin foams; woven materials, such as woven polypropylene, polyethylene or polyester fabrics; and composites and laminates of the above nonwoven, film, foam, and woven materials.

In one embodiment of the present invention, the first and second sheets 42, 44 of containment flap material are non-integrally formed. That is, the first and second sheets of containment flap material represent separate elements which are Joined in a superposed relationship. Specifically, the first and second sheets of containment flap material are not formed from an integral piece of material through a folding process. In another embodiment of the present invention, the first and second sheets of containment flap material are integrally formed. That is, the first and second sheets of containment flap material are formed from a single, integral piece of material through a folding process in which the single piece of material is folded upon itself to form two layers which comprise the first and second sheets of containment flap material.

In another specific embodiment, the first and second sheets of containment flap material are formed from a nonwoven material, such as a spunbond or meltblown polyethylene or polypropylene material. When it is desired to provide a containment flap assembly which is generally liquid pervious, the spunbond material will suitably be treated with a surfactant to render it generally hydrophilic.

In one specific embodiment, the first and second sheets of containment flap material comprise a polypropylene spunbond material having a basis weight of about 0.4 ounce per square yard (14.0 grams per square meter) and being formed from fibers having a denier of about 2.5–3.8 d, which material is treated with a surfactant commercially available from Rohm and Haas Company, Philadelphia, Pa., under the trade designation Triton X-102, at an add-on rate of about 0.3 weight percent.

The first and second elastic members 32 and 40 may comprise any elastomeric material capable of being elongated at least about 50 percent, alternately at least about 250 percent, alternately at least about 350 percent, and capable of recovering to a length within at least about 75 percent, more particularly, at least about 50 percent of its elongated length (original length plus elongation). The first and second elastic members may be in the form of ribbons, individual strands, or other configurations. In one embodiment, the elastic members are in the form of individual elastomeric threads of elastomeric material. As described above, the inner and outer containment flaps may comprise a single, elastic member or two or more elastic members. In one specific embodiment, the first and second elastic members comprises a 470 decitex LYCRA® thread commercially available from E. I. Dupont de Nemours and Co. Alternatively, the first and second elastic members can be composed of a thermoplastic elastomer or a natural or synthetic rubber commercially available from J. P. S. Elastomerics Corp. The first and second elastic members can also be composed of a heat-activatable elastic material such as PEBAX® elastic material, commercially available from Atochem, Inc., which can be activated with heat-treatment after attachment to the containment flap.

In one embodiment, the first and second elastic members are adhesively attached to the first sheet of containment flap material in a pretensioned condition. Those skilled in the art will recognize that a wide variety of adhesive materials are suitable for use in the present invention. Specifically, the adhesive may comprise a hot melt adhesive, a pressure-sensitive adhesive, latex adhesive, and the like. In one specific embodiment, the adhesive comprises a hot melt adhesive commercially available from Findley Adhesives, Inc. under the trade designation H2096. The adhesive may be applied in a wide variety of patterns known to those skilled in the art. Specifically, the adhesive may be applied in swirls, strands, strips, bars, spots, and the like, and may be applied via slot coating, spraying, printing, and the like. Those skilled in the art will appreciate other methods of attaching the first and second elastic members to the first sheet of containment flap material. Other suitable methods include thermal bonding, ultrasonic bonding, infrared bonding, radio frequency bonding, and the like. The same methods and materials may be employed to join the second sheet of containment flap material to the first sheet of containment flap material.

Attachment of the first and second elastic members to the first sheet of containment flap material in a pretensioned condition allows the elastic members to contract and gather the first and/or second sheets of containment flap material when they have been allowed to elastically contract. This foreshortens the distal edge of the containment flap and causes it to be positioned away from the proximal edge of the containment flap.

Bodyside liner 20 suitably presents a body-facing surface which is compliant, soft feeling, and non-irritating to the wearer's skin. Further, bodyside liner 20 may be less hydrophilic than the absorbent core 22, to present a relatively dry surface to the wearer, and is sufficiently porous to be liquid permeable, permitting liquid to readily penetrate through its thickness. A suitable bodyside liner may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Bodyside liner 20 is suitably employed to help isolate the wearer's skin from liquids held in absorbent core 46.

Various woven and nonwoven fabrics can be used for bodyside liner 20. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant, or otherwise processed, to impart a desired level of wettability and hydrophilicity. In a particular embodiment of the present invention, the bodyside liner 20 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

The outer cover 18 may suitably be composed of a material which is either liquid permeable or liquid impermeable. It is generally preferred that the outer cover 18 be formed from a material which is substantially impermeable to liquids. For example, a typical outer cover can be manufactured from a thin plastic film or other flexible liquid-impermeable material. For example, the outer cover 18 may be formed from a polyethylene film having a thickness of from about 0.012 millimeter (0.5 mil) to about 0.051 millimeter (2.0 mils). If it is desired to present the outer cover 18 with a more clothlike feeling, the outer cover 18 may comprise a polyethylene film having laminated to the outer surface thereof a nonwoven web, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover may be formed of a woven or nonwoven fibrous web layer which has been totally or partially constructed or treated to impart a desired level of liquid impermeability to selected regions that are adjacent or proximate the absorbent core 22. Still further, the outer cover 18 may optionally be composed of a micro-porous "breathable" material which permits vapors to escape from the absorbent core 22 while still preventing liquid exudates from passing through the outer cover 18.

The absorbent core 22 suitably comprises a matrix of hydrophilic fibers, such as a web of cellulosic fluff, mixed with particles of a high-absorbency material commonly known as superabsorbent material. In a particular embodiment, absorbent core 22 comprises a mixture of superabsorbent hydrogel-forming particles and wood pulp fluff. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed.

Alternatively, the absorbent core may comprise a laminate of fibrous webs and superabsorbent material or other suitable means of maintaining a superabsorbent material in a localized area.

The absorbent core 22 may have any of a number of shapes. For example, the absorbent core may be rectangular, I-shaped or T-shaped. It is generally preferred that the absorbent core be narrower in the crotch portion than the rear or front portion.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble, but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic, absorbent gelling polymers are disclosed in U.S. Pat. No. 4,076,663 issued Feb. 28, 1978, to Masuda et al. and U.S. Pat. No. 4,286,082 issued Aug. 25, 1981, to Tsubakimoto et al.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like.

As a general rule, the high-absorbency material is present in the absorbent core in an amount of from about 5 to about 100 weight percent based on total weight of the absorbent core.

The outer cover 18 and bodyside liner 20 are generally adhered to one another so as to form a pocket in which the absorbent core 22 is located. Thus, leg cuffs 23 are suitably formed by portions of the outer cover 18, and/or bodyside liner 20, which extend beyond the longitudinal sides of the absorbent core 22. Naturally, the leg cuffs 23 can also be formed from separate materials which are attached to the outer cover 18 and/or bodyside liner 20.

Leg cuffs 23 include leg elastics. Materials suitable for use in forming the leg elastics are known to those skilled in the art. Exemplary of such materials are strands or ribbons of a polymeric, elastomeric material, which are adhered to the diaper at the leg cuff while in a stretched position, or which are attached to the diaper while the diaper is pleated, such that elastic constrictive forces are imparted to the leg cuff 23.

A wide variety of other diaper configurations, as well as training pants, incontinence garments, and like configurations, are suitable for use in the present invention. Diapers suitable for use in the present invention are described in greater detail in commonly assigned U.S. patent application Ser. No. 08/096,654 entitled, "Thin Absorbent Article Having Rapid Uptake of Liquid," filed Jul. 22, 1993 (as a continuation of Ser. No. 757,760, filed Sep. 11, 1991), in the names of Hanson et al., now U.S. Pat. No. 5,509,915, issued Apr. 23, 1996; and U.S. Pat. No. 5,192,606 issued Mar. 9, 1993, to Proxmire et al.

In another aspect, the present invention concerns a method for producing an absorbent garment. The steps of the method comprise:

A. providing a first integral sheet of containment flap material;

B. attaching a pair of first elastic members to said first sheet of containment flap material;

C. attaching a pair of second elastic members to said first sheet of containment flap material, said pair of second elastic members being generally inboard of such pair of first elastic members;

D. removing a portion of said first sheet of containment flap material between said pair of second elastic members to form a containment flap assembly; and E. attaching said containment flap assembly to a garment chassis to define outer containment flaps having a proximal edge and a distal edge and inner containment flaps having a proximal edge and a distal edge, said garment chassis comprising an outer cover, a bodyside liner, and an absorbent core located between said outer cover and said bodyside liner.

Figure 8:
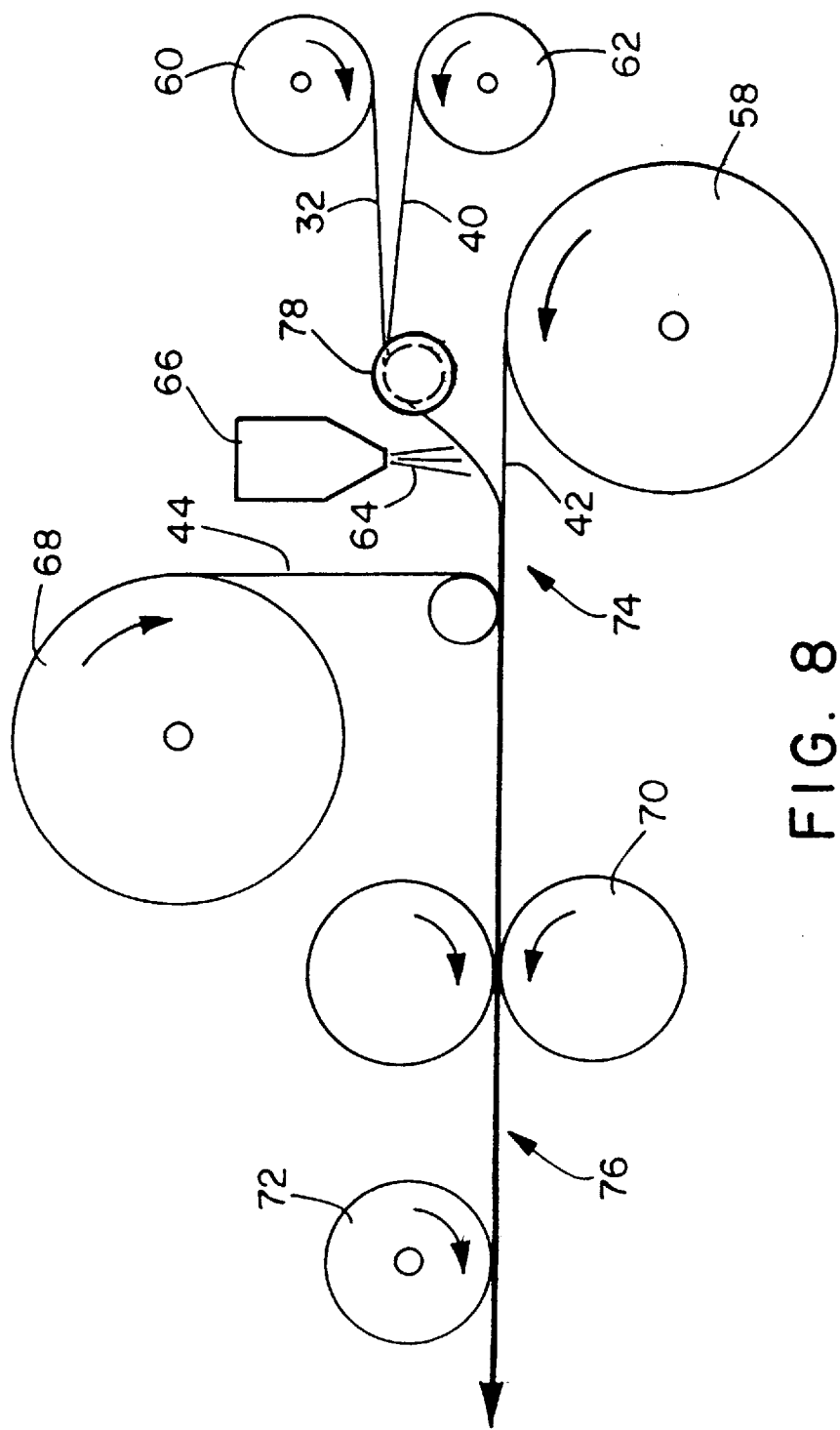
FIG. 8 illustrates a schematic view of a method according to the present invention.
Figure 9:
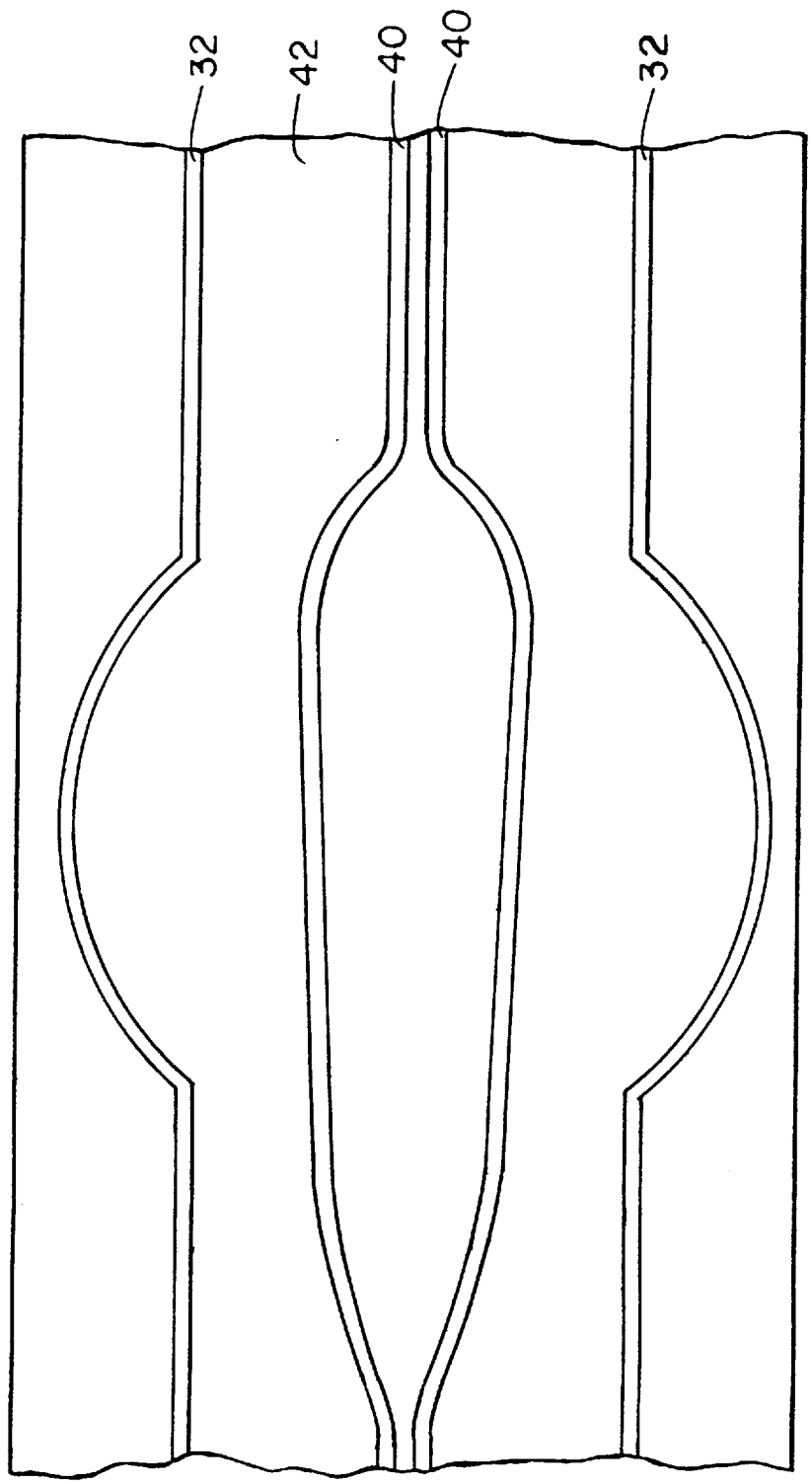
FIG. 9 illustrates an intermediate product produced by the method illustrated in FIG. 8.
Figure 10:
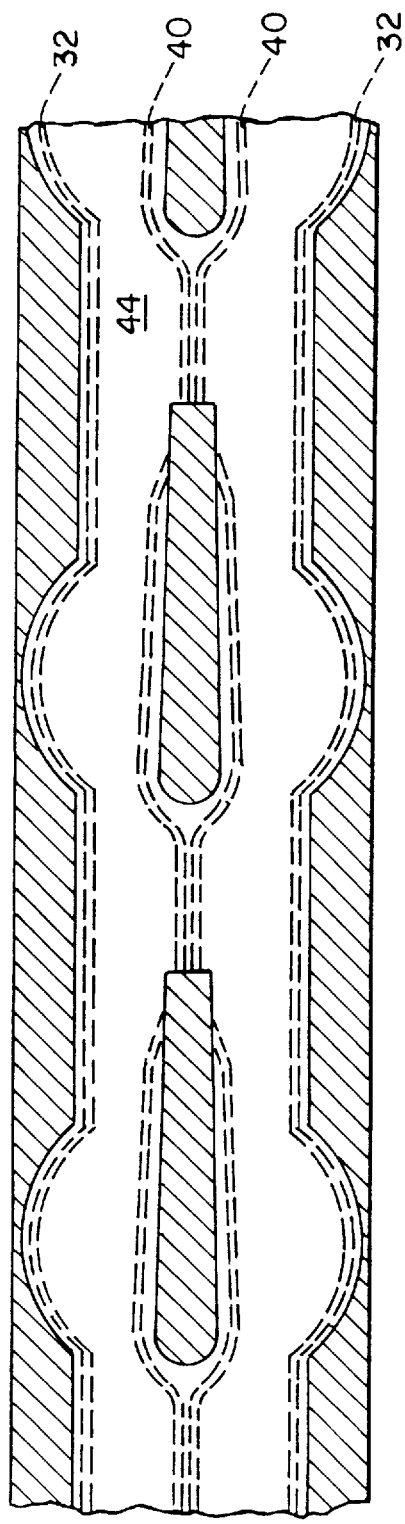
FIG. 10 illustrates an intermediate product produced by the method illustrated in FIG. 8.

The steps of the method can best be understood by reference to FIG. 8 which is a schematic illustration of a method according to the present invention. A first sheet of containment flap material 42 is provided from first supply roll 58. A pair of first elastic members 32 are provided from second supply roll 60. A pair of second elastic members 40 are supplied from third supply roll 62. The first and second elastic members are attached to the first sheet of containment flap material by adhesive 64 supplied by adhesive supply means 66. The pair of second elastic members are located inboard of the pair of first elastic members as described above. A second sheet of containment flap material 44 is supplied from fourth supply roll 68 and is attached to the first sheet of containment flap material so as to locate the elastic members between the first and second sheets of containment flap material. The combination of first and second sheets of containment flap material and first and second elastic members passes through a pair of nip rollers 70. A cutter 72 removes a portion of the first and second sheet of containment flap material, between the pair of second elastic members, to define an opening 46 and to form a containment flap assembly. The containment flap assembly is subsequently attached to a garment chassis to define outer containment flaps and inner containment flaps as described in connection with FIGS. 1–7. This step is not illustrated in FIG. 8. The garment chassis comprises an outer cover, a bodyside liner and an absorbent core located between said outer cover and said bodyside liner. The components of the garment chassis are as described above in connection with diaper 10. FIG. 9 illustrates an intermediate product existing at location 74 in FIG. 8. FIG. 10 illustrates an intermediate product existing at location 76 in FIG. 8. The cross-hatched areas illustrated in FIG. 10 will be removed by cutter 72 to produce the containment flap assembly 24 illustrated in FIGS. 1–7. That is, a portion of the first and second sheets of containment flap material outboard of said first elastic members will be removed.

Materials suitable for use as the first and second sheets of containment flap material, and first and second elastic members, are as described above in connection with the disposable diaper 10 illustrated in FIGS. 1–7. Methods of positioning the first and second elastic members in the configuration illustrated in the drawings include positioning means 78 which suitably include cams, mechanical arms, pneumatic arms, grooved patterned rolls, and the like. Methods of attaching the first and second elastic members to the first sheet of containment flap material are as described above. In the illustrated embodiment, the first and second elastic members are adhesively attached to the first sheet of containment flap material.

Cutter 72 may include devices such as water cutters, die cutters, slitters, ultrasonic cutters, laser cutters, and the like. The cross-hatch material illustrated in FIG. 10 as being removed by cutter 72 may be removed in a single cutting operation or may be sequentially removed through a series of cutting operations which may be the same or different. The containment flap assembly is then attached to the garment chassis as described above in connection with diaper 10.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of producing an absorbent garment having a front portion, a rear portion and a crotch portion between said front portion and said rear portion, the steps of the method comprising:

providing a first integral sheet of containment flap material;

attaching a pair of first elastic members to said first sheet of containment flap material;

attaching a pair of second elastic members to said first sheet of containment flap material, said pair of second elastic members being generally inboard of said first elastic members;

removing a portion of said first sheet of containment flap material between said pair of second elastic members to form a containment flap assembly; and attaching said containment flap assembly to a garment chassis to define a pair of outer containment flaps each having a proximal edge and a distal edge with one of said first elastic members adjacent said distal edge and a pair of inner containment flaps having a proximal edge and a distal edge with one of said second elastic members adjacent said distal edge, said garment chassis comprising an outer cover, a bodyside liner, and an absorbent core located between said outer cover and said bodyside liner.

2. The method according to claim 1 wherein only a portion of the first sheet of containment flap material between said pair of second elastic members is removed.

3. The method according to claim 2 further comprising the step of attaching a second sheet of containment flap material to said first sheet of containment flap material after said pairs of first and second elastic members are attached to the first sheet of containment flap material and before said removal of said portion of said first sheet of containment flap material.

4. The method according to claim 3 wherein a portion of said second sheet of containment flap material between said pair of second elastic members is removed.

5. The method according to claim 1 wherein said pair of first elastic members is non-parallel.

6. The method according to claim 1 wherein said pair of second elastic members is non-parallel.

7. The method according to claim 5 wherein said pair of second elastic members is non-parallel.

8. The method according to claim 6 wherein said pair of second elastic members is spaced further apart in said crotch portion than in said rear portion.

9. The method according to claim 8 wherein said second elastic members are adjacent one another in said rear portion.

10. The method according to claim 1 further comprising the steps of removing a portion of said first sheet of containment flap material outboard of said first pair of elastic members.

11. The method according to claim 3 further comprising the steps of removing a portion of said first and second sheets of containment flap material outboard of said first pair of elastic members.

12. The method according to claim 1 wherein said containment flap assembly is attached to said garment chassis along two lines of attachment, said lines of attachment defining the proximal edges of said outer and inner containment flaps.

13. A method of producing an absorbent garment having a front portion, a rear portion, and a crotch portion between said front portion and said rear portion, the steps of the method comprising:

providing a first integral sheet of containment flap material;

attaching a pair of first elastic members to said first sheet of containment flap material;

attaching a pair of second elastic members to said first sheet of containment flap material, said pair of second elastic members being generally inboard of said pair of said first elastic members;

attaching a second sheet of containment flap material to said first sheet of containment flap material such that the pair of first elastic members and the pair of second elastic members are located between said first and second sheets of containment flap material;

removing a portion of said first and second sheets of containment flap material between said pair of second elastic members to form a containment flap assembly; and attaching said containment flap assembly to a garment chassis to define a pair of outer containment flaps each having a proximal edge and a distal edge with one of said first elastic members adjacent said distal edge and a pair of inner containment flaps each having a proximal edge and a distal edge with one of said second elastic members adjacent said distal edge, said garment chassis comprising an outer cover, a bodyside liner, and an absorbent core located between said outer cover and said bodyside liner.

* * * * *

UNITED STATES PATENT AND TRADEMARK OFFICE
CERTIFICATE OF CORRECTION

PATENT NO.   : 5,824,172
DATED        : October 20, 1998
INVENTOR(S)  : David P. Kielpikowski It is certified that error appears in the above-identified patent and that said Letters Patent is hereby corrected as shown below:

In claim 1, line 20, please insert --each-- before "having".

Signed and Sealed this

Tenth Day of April, 2001

NICHOLAS P. GODICI

*Attest:*

*Attesting Officer*   *Acting Director of the United States Patent and Trademark Office*